(12) United States Patent
Zdeblick et al.

(10) Patent No.: US 6,383,191 B1
(45) Date of Patent: May 7, 2002

(54) LAPAROSCOPIC INSTRUMENT SLEEVE

(75) Inventors: Thomas Zdeblick, Middletown, WI (US); Thomas V. McGahan, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/526,000

(22) Filed: Mar. 15, 2000

(51) Int. Cl.[7] .............................................. A61B 17/90
(52) U.S. Cl. ........................................ 606/105; 606/90
(58) Field of Search .............................. 606/90, 96, 99, 606/104, 105, 108; 623/17.16

(56) References Cited

U.S. PATENT DOCUMENTS

| | | |
|---|---|---|
| 4,795,426 A | 1/1989 | Jones |
| 5,073,169 A | 12/1991 | Raiken |
| 5,176,649 A | 1/1993 | Wakabayashi |
| 5,217,001 A | 6/1993 | Nakao et al. ................... 128/4 |
| 5,354,302 A * | 10/1994 | Ko ............................. 606/104 |
| 5,359,995 A | 11/1994 | Sewell, Jr. .................... 128/20 |
| 5,385,561 A * | 1/1995 | Cerny ......................... 604/264 |
| 5,391,156 A | 2/1995 | Hildwein et al. ........... 604/174 |
| 5,404,870 A | 4/1995 | Brinkerhoff et al. |
| 5,490,843 A | 2/1996 | Hildwein et al. ........... 604/164 |
| 5,562,677 A | 10/1996 | Hildwein et al. ........... 606/108 |
| 5,772,680 A | 6/1998 | Kieturakis et al. .......... 606/190 |
| 5,803,921 A | 9/1998 | Bonadio ........................ 606/1 |
| 5,807,402 A | 9/1998 | Yoon ........................... 606/185 |
| 5,814,058 A | 9/1998 | Carlson et al. ............. 606/185 |
| 5,814,073 A | 9/1998 | Bonutti |
| 5,830,191 A | 11/1998 | Hildwein et al. ........... 604/175 |
| 5,865,727 A * | 2/1999 | Sano et al. ................... 600/178 |
| 6,004,326 A * | 12/1999 | Castro et al. .................. 606/99 |
| 6,015,421 A | 1/2000 | Echeverry et al. .......... 606/190 |
| 6,113,602 A * | 9/2000 | Sand ............................ 606/61 |
| 6,126,633 A * | 10/2000 | Kaji et al. ................ 604/95.04 |
| 6,171,339 B1 * | 1/2001 | Houfburg et al. ............. 623/17 |

FOREIGN PATENT DOCUMENTS

| | | |
|---|---|---|
| WO | WO 97/30666 | 8/1997 |
| WO | WO 99/52577 | 10/1999 |

* cited by examiner

Primary Examiner—Todd E. Manahan
Assistant Examiner—David C Comstock
(74) Attorney, Agent, or Firm—Woodard, Emhardt, Naughton, Moriarty & McNett

(57) ABSTRACT

Surgical techniques and instruments are provided for performing laparoscopic surgical procedures. The apparatus includes a sleeve having a proximal end, a distal end, and a lumen extending between the proximal and distal ends. The lumen opens at the proximal end and receives an elongated member, such as a cannula or surgical instrument, therethrough. The sleeve is resilient material and conformable to the outer shape of at least a distal portion of the elongate member. In one form the distal end wall includes means for opening the end wall to allow the elongate member to advance therethrough. The sleeve may also be provided with internal ribs and a flange member. Various techniques using various surgical instruments in laparoscopic procedures are also disclosed.

60 Claims, 5 Drawing Sheets

LAPAROSCOPIC INSTRUMENT SLEEVE

BACKGROUND OF THE INVENTION

The present invention relates generally to methods and instruments for performing spinal surgery. Specifically, the invention concerns to a sleeve for use with laparoscopic techniques and instruments in spinal surgeries.

Various surgical techniques and instruments have been developed for use in laparoscopic procedures to develop an anatomic space and to permit visualization of the procedures. For example, PCT International Publication No. WO 97/30666 to Zdeblick et al. discloses laparoscopic surgical techniques and instruments for preparing a spinal disc space for implantation of fusion devices or implants. The laparoscopic instrumentation provides a sealed working channel to the disc space through which the disc space is distracted, the vertebral endplates and surrounding discs are reamed, and the vertebral implant inserted, all through a laparoscopic port engaged to the end of the sleeve. In this technique, the instrumentation is placed directly through the tissue through an incision in the skin. One drawback associated with this technique is that the instrumentation has edges, corners or the like that can snag or catch tissue as it is advanced therethrough, increasing tissue trauma and bleeding as a result of the procedure. Another drawback associated with this technique is that although the instrumentation is provided with a sealed working channel, the space between the tissue and the instrument provides an avenue for loss of insufflation pressure.

While the above described instruments and procedures represent various approaches over prior surgical instruments and procedures for spinal surgery, the need for improvements remains. In particular, procedures and instruments are needed that minimize trauma to tissue surrounding the surgical site while allowing surgical procedures to be performed. Also needed are instruments and techniques that maintain the sealed environment of the working space during surgical procedures. The present invention is directed to these needs, among others.

SUMMARY OF THE INVENTION

The present invention includes a sleeve that is conformable to a surgical instrument and facilitates insertion of the instrument through tissue during a laparoscopic procedure.

In accordance with one aspect of the present invention there is provided an apparatus for performing laparoscopic surgical procedures through a tissue opening in a patient. The apparatus includes an elongate member with a length having an outer shape along its length. The apparatus also includes a substantially non-expandable sleeve having a proximal end, a distal end wall, and a lumen extending therebetween opening at the proximal end to receive the elongate member. The sleeve is resilient and conformable to the outer shape of at least a distal portion of the elongate member.

In another aspect of the present invention there is provided an apparatus for performing laparoscopic surgical procedures through a tissue opening in a patient. The apparatus includes an elongate member having an outer shape along its length. The apparatus also includes a sleeve with a proximal end, a distal end, and an inner wall defining a lumen extending therebetween. The lumen opens at the proximal end and receives the elongate member. The sleeve is resilient and conformable to the outer shape of at least a distal portion of the elongate member. The sleeve also includes at least one rib extending from the inner wall into the lumen. In a preferred form the at least one rib extends along at least a portion of the length of the sleeve.

In a further aspect of the present invention an apparatus for performing laparoscopic surgical procedures through a tissue opening in a patient is provided. The apparatus includes an elongate member having an outer shape along its length. The apparatus also includes a sleeve having a proximal end, a distal end wall, and an inner wall defining a lumen extending between the proximal and distal ends. The lumen opens at the proximal end to receive the elongate member and is conformable to the outer shape of at least a distal portion of the elongate member. The distal end wall of the sleeve includes means for opening the end wall to allow extension of the elongate member therethrough.

In yet a further aspect of the present invention, there is provided an apparatus for performing laparoscopic surgical procedures through a tissue opening in a patient. The apparatus includes an elongate member having an outer shape along its length. The apparatus includes a sleeve with a proximal end, a distal end, and an inner wall defining a lumen extending between the proximal end and the distal end. The lumen opens at the proximal end to receive the elongate member. A flange member has an opening slidably and sealingly receiving the sleeve member therethrough. The flange member is positionable against the tissue of the patient to seal the tissue opening.

In accordance with a further aspect of the invention, there is provided a method for performing a laparoscopic spinal surgical procedure through skin and tissue of a patient. The method includes: incising the skin and tissue of the patient; providing an elongate member with a length extending between a distal end and a proximal end, the elongate member having an outer shape along its length, and a sleeve having a proximal end, a distal end wall, and a lumen extending therebetween opening at the proximal end receiving at least a distal portion of the elongated member, the sleeve being substantially made from a resilient material and conformable to the outer shape of at least the distal portion of the elongate member; providing a flange member having a central opening receiving the sleeve therethrough; placing the flange member on the skin; and advancing the elongate member and sleeve through the flange member and through the incision to the spine while the sleeve provides a barrier between the tissue and the elongate member. In one form, the flange member seals the space between the tissue and the sleeve.

In accordance with another aspect of the present invention, a method for performing a laparoscopic surgical procedure at a location in a patient is provided. The method includes incising the tissue of the patient; providing an elongate member with a length extending between a distal end and a proximal end, the elongate member having an outer shape along its length, and a sleeve having a proximal end, a distal end wall, and a lumen extending therebetween opening at the proximal end receiving at least a distal portion of the elongate member, the sleeve being resilient and conformable to the outer shape of at least the distal portion of the elongate member; advancing the elongate member and sleeve through the tissue to a position adjacent the location; and advancing the elongate member through the distal end wall of the sleeve to the location.

Other objects, advantages, features, embodiments, aspects and benefits can be discerned from the following written description and the accompanying figures.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated herein are contemplated as would normally occur to one skilled in the art to which the invention relates.

Figure 1:
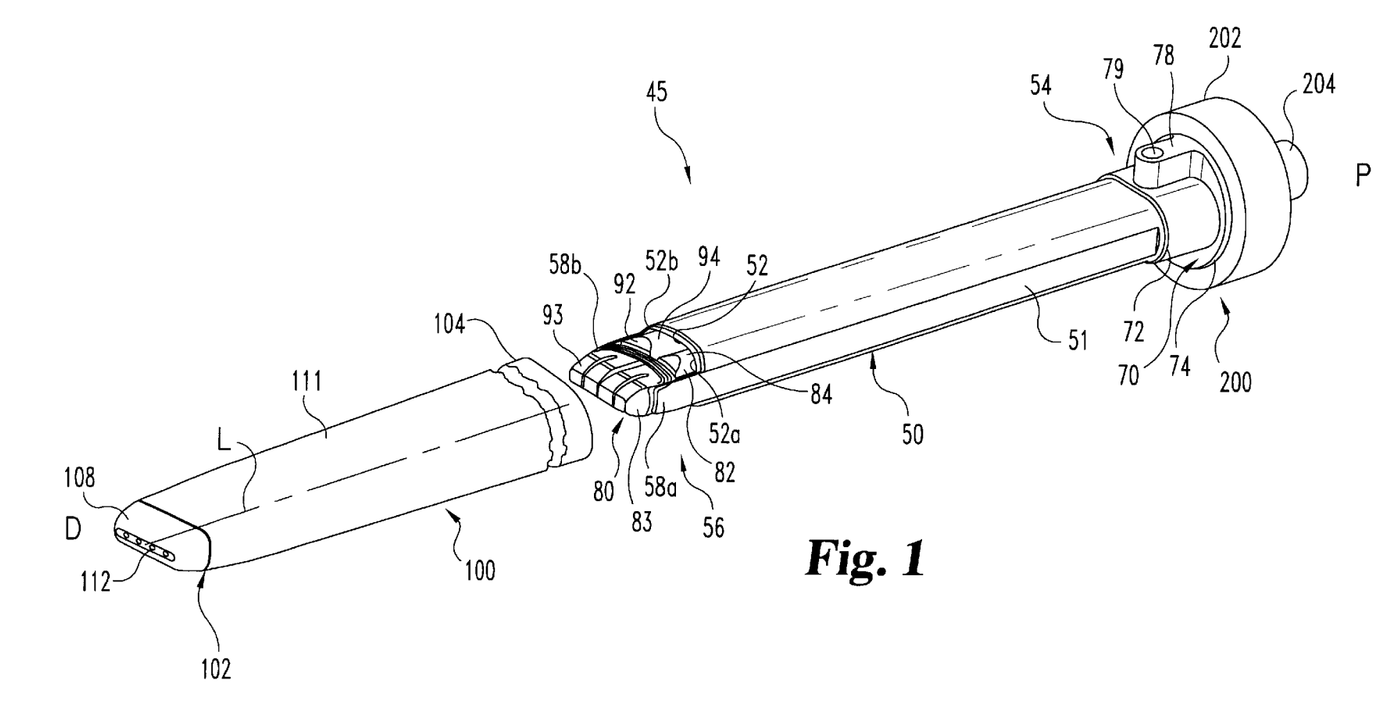
FIG. 1 is a perspective view looking proximally at a surgical apparatus according to one aspect of the present invention.

A surgical apparatus in accordance with the present invention is illustrated in FIG. 1 and designated generally at 45. Surgical apparatus 45 is particularly useful for anteriorly accessing and preparing, as show in FIG. 2, a disc space S via a laparoscopic approach for insertion of vertebral implants or fusion devices between upper vertebral member V1 and lower vertebral body V2. In one aspect of the present invention, the surgical apparatus allows surgical procedures to be performed under a relatively sealed and protected insufflated environment within the body cavity. This prevents leakage of abdominal distension fluids into the working channel and disc space and aids in visualization of the surgical site. The surgical procedure described herein is performed via an anterior approach to the spine. However, the surgical instruments of the present invention are not limited to such an approach, and may find application in lateral, antero-lateral, posterior, and postero-lateral approaches as well. Additionally, the surgical apparatus of the present invention includes sleeve 100 having application with all types of surgical instruments and in areas other than spinal surgery.

Figure 3:
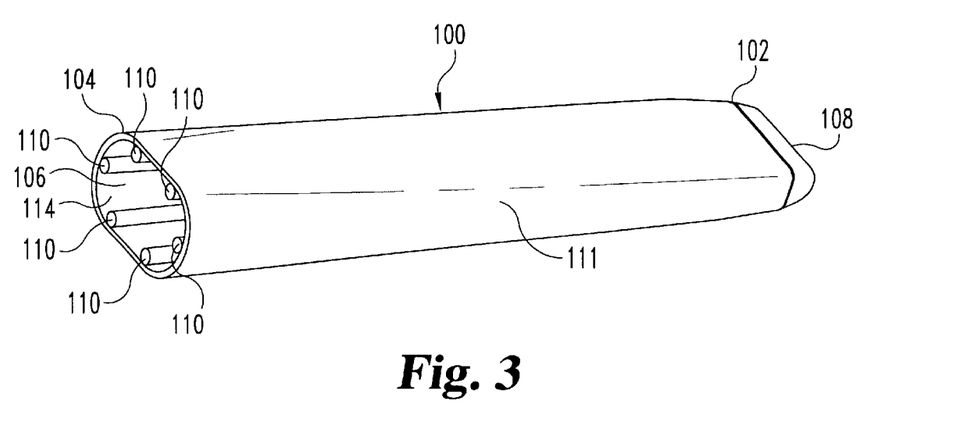
FIG. 3 is a perspective view looking distally at the sleeve comprising a portion of the apparatus of FIG. 1.

Referring now to FIGS. 1 and 3, apparatus 45 includes sleeve 100 having a distal end 102, a proximal end 104, and a lumen 106 extending therebetween along longitudinal axis L. Sleeve 100 further includes distal end wall 108 and, in the illustrated embodiment, includes perforation or holes 112 in distal end wall 108. A number of ribs 110 are provided on inner wall 114 of sleeve 100 and extend into lumen 106. In the illustrated embodiment, six ribs 106 are provided. Preferably, ribs extend with longitudinal axis L along at least a portion of the length of sleeve 100. Sleeve 100 receives in lumen 106 at least a distal end portion of an elongated member, such as a surgical instrument, tunneling device, or cannula as described further below. Sleeve 100 is made from a resilient material allowing sleeve 100 to assume its shape of FIG. 1 when the elongated member is removed. Inner wall 114 has a shape that conforms with the shape of the elongated member placed in lumen 106 to provide a snug fit. Sleeve 114 can preferably stretch to accommodate the elongated member if necessary. Ribs 110 facilitate sliding advancement of the elongated member in sleeve 100 by reducing the contact surface area between sleeve 100 and the elongated member.

Sleeve 100 is made from non-rigid material that will not catch or snag skin and tissue of the patient as sleeve 100 and the elongated member placed therein are advanced to the surgical location. Sleeve 100 covers any sharp edges, protrusions, or other portions of the member, allowing the elongated member to be advanced through the tissue with the tissue protected by sleeve 100. In one embodiment, sleeve 100 is made from silicone. Other embodiments contemplate that sleeve 100 is made from latex or other suitable elastomeric material. In one embodiment, sleeve 100 has a wall thickness such that sleeve 100 is substantially non-expandable, the wall thickness providing resistance to tearing and puncturing of sleeve 100 by the elongated member during insertion. When sleeve 100 and the elongated member are positioned adjacent the surgical location, the elongated member can be advanced through distal end wall 108 of sleeve 100 to the surgical location in order to perform the desired surgical procedure. Perforations 112 facilitate the opening of end wall 108 as the member is pushed therethrough. Sleeve 100 can also be tapered to increase in cross-section from distal end 102 to proximal end 104 to further facilitate penetration and insertion through the skin and tissue and withdrawal of sleeve 100.

It is contemplated that end wall 108 is frangible and in lieu of perforations 112 could be provided with an opening that is seamed, glued or otherwise fastened to a closed condition for insertion and opened upon advancement of the elongated member. In another form, end wall 108 is includes a reduced thickness portion that is penetrable by the elongated member. Other forms contemplate an open distal end wall 108. It is further contemplated that sleeve 100 could be provided without ribs 110, and inner wall 114 of sleeve 100 directly contacts the elongated member. It is contemplated in further embodiments that a friction reducing coating or material may be included with inner wall 114 to facilitate relative movement between the elongated member and sleeve 100.

Referring now to FIGS. 4–7, a further aspect of the present invention will be described reference to surgical apparatus 45'. A flange member 150 is provided with an opening 152 therethrough for receiving sleeve 100 and maintaining a relatively sealed environment between sleeve 100 and the tissue. Flange member 150 includes a corrugated portion 154 about opening 152 and a bearing portion 156 extending outwardly from corrugated portion 154. In the illustrated embodiment, bearing portion 156 is in the form of a flat plate that rests against the skin of the patient. Bearing portion 156 can be stapled or otherwise secured to the skin and/or be provided with openings for sutures or other fasteners.

Corrugated portion 154 is preferably flexible, allowing sleeve 100 and the elongate member placed through opening 152 to be universally pivoted therein as indicated by the arrows R as the sleeve 100 is advanced therethrough. The flexible corrugated portion 154 maintains contact between wall portion 158 and sleeve 100 during pivoting and insertion to maintain the relatively sealed condition between sleeve 100 and the tissue and preventing loss of insufflation pressure around sleeve 100. It is further contemplated that an O-ring can be provided around wall portion 158 to further maintain the sealed condition.

Figures 4, 5:
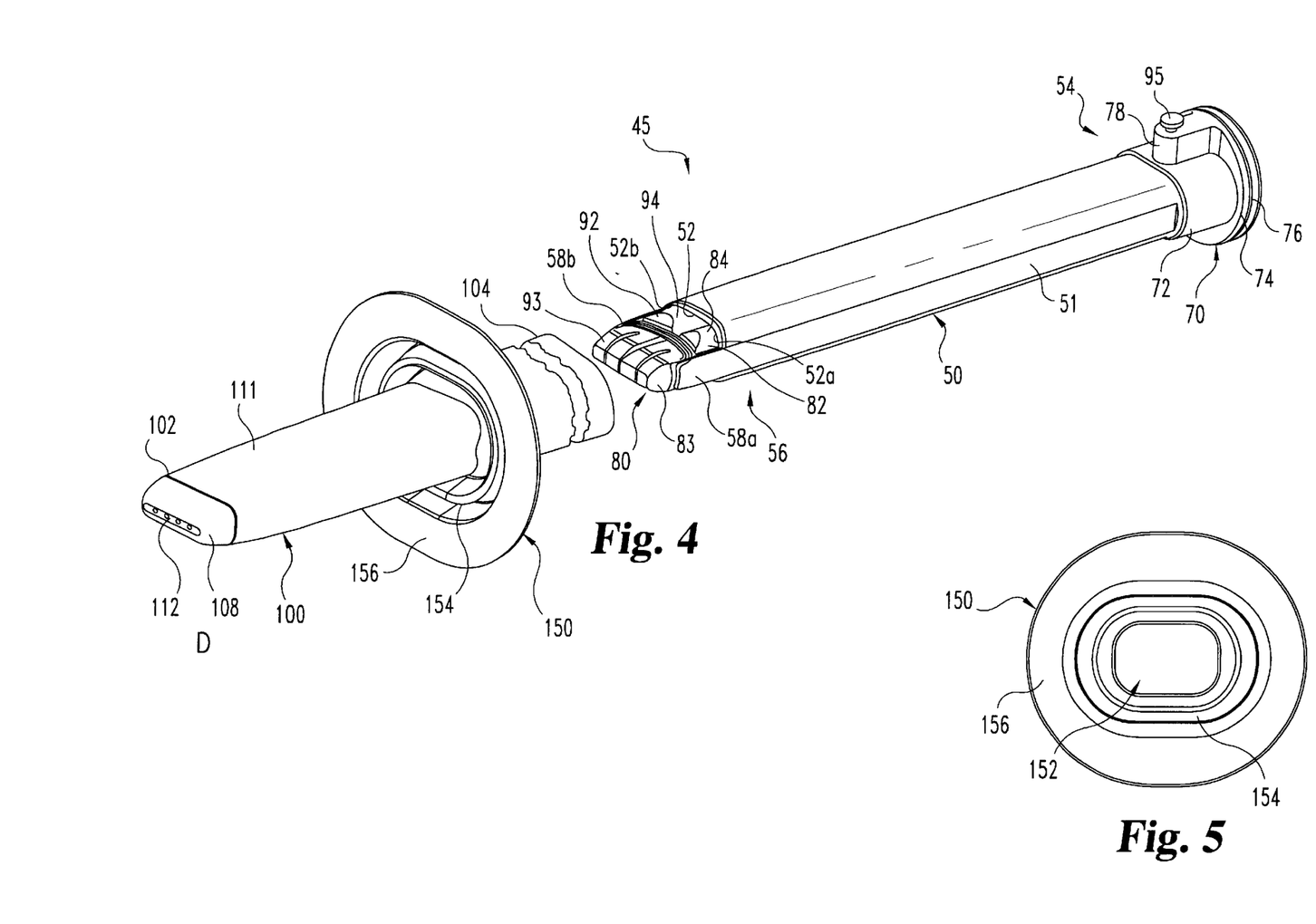
FIG. 4 is a perspective view looking proximally at the surgical apparatus of FIG. 1 with the sleeve inserted through a flange member and the cap member removed.
FIG. 5 is a left-hand end view of the flange member of FIG. 4.
Figure 6:
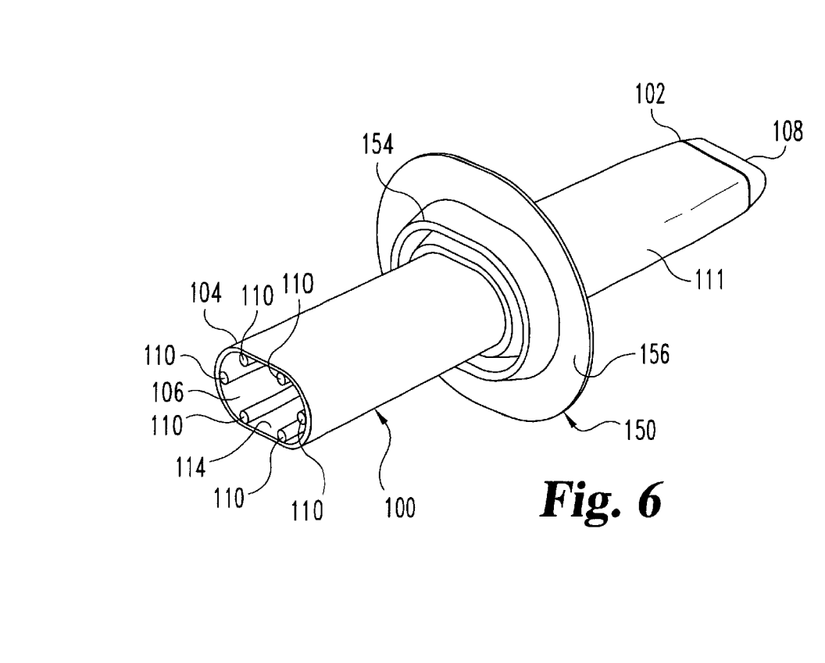
FIG. 6 is a perspective view looking distally at the sleeve and flange member of FIG. 4.
Figure 7:
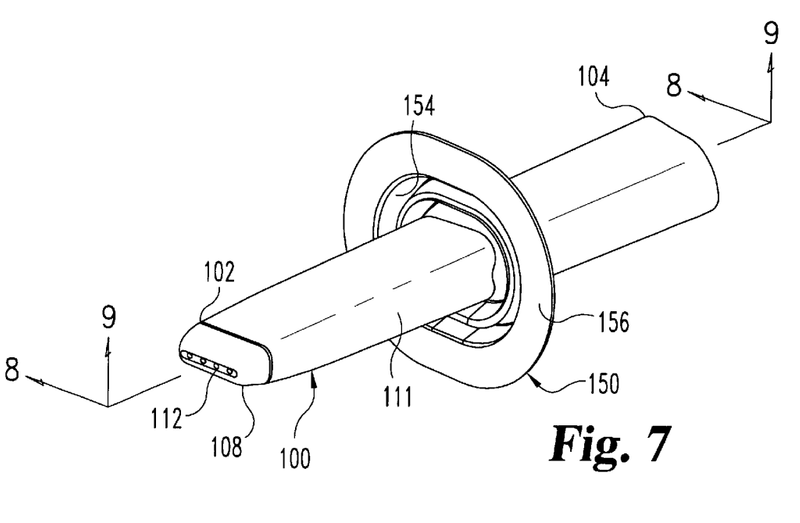
FIG. 7 is a perspective view looking proximally at the sleeve and flange member of FIG. 4.

In the specific embodiments of surgical apparatus 45 and 45' illustrated in FIGS. 1 and 4, respectively, there is provided an elongated tunneling or insertion member in the form of cannula 50 and distractor assembly 80. In the description that follows, proximally refers to the direction indicated by letter "P" and distally refers to the direction indicated by letter "D." In the illustrated embodiment, cannula 50 has an inner working channel 52 extending between proximal end 54 and distal end 56 with distractor assembly 80 disposed in working channel 52. A cap member 200 is secured to a flange ring 70 at proximal end 54. The cannula 50, distractor assembly 80, and cap member 200 are similar to those described in pending U.S. patent application Ser. No. 09/525,972, filed Mar. 15, 2000, entitled Methods and Instruments for Laparoscopic Surgery, which is incorporated herein by reference in its entirety. However, it should be understood that the present invention contemplates that the present invention also has application with other types of elongated members, including trocars, cannulas, viewing instruments, cutting instruments, dilators, distractors or distractor assemblies, or other instruments inserted through skin and tissue to a location in a patient. Cannula 50 receives various tools and surgical instruments therethrough in order to perform surgical procedures at the location in the patient.

In a preferred form, cannula 50 has a length sufficient to extend from the spine through the skin of the patient in order to allow the surgeon access to the spine. Cannula 50 includes opposite fingers 58a and 58b extending from distal end 56. Fingers 58a, 58b can be sized according to the desired height of the particular disc space and the depth of the disc space into which cannula 50 is to be inserted. Fingers 58a, 58b maintain the spacing between the adjacent vertebrae during surgical procedures, prevent surrounding tissue and vasculature from migrating into the disc space, and protect surrounding tissue and vasculature during surgical procedures. In addition, fingers 58a, 58b can be tapered or rounded along all or a portion of their length in order to conform to a normal angle between adjacent vertebrae at the instrumented level. In one alternate form, fingers 58a, 58b distract the disc space during insertion therein in lieu of distractor assembly 80. In another form, cannula 50 is provided without fingers 58a, 58b.

Cannula 50 has a wall 51 forming a non-circular perimeter. In the illustrated embodiment, wall 51 has a racetrack shaped perimeter. Other shapes for the perimeter of wall 51 are also contemplated, including circular, elliptical, rectangular, or other as would occur to those skilled in the art. Working channel 52 includes a first portion 52a and an adjacent second portion 52b. The illustrated embodiment of cannula 50 has a reduced profile that minimizes the width of channel 52 between fingers 58a, 58b while, as described further below, providing for bilateral implant insertion. Other shapes for working channel 52 are also contemplated, including a circular working channel not having first and second portions; elliptical, racetrack shaped, square, or rectangular working channels; working channels formed by adjacent circular cannulas; and other working channel shapes as would occur to those skilled in the art.

Distractor assembly 80 includes a first distractor 82 and a second distractor 92 for distracting a spinal disc space disposed in working channel 52. Distractors 82 and 92 include distractor tips 83 and 93, respectively, positioned between first distraction finger 58a and second distraction finger 58b extending from distal end 56. Distractors 82 and 92 also include shafts 84 and 94, respectively, extending through working channel 52 to proximal end 54 of cannula 50. Other variations and forms of distractor assembly 80 are also contemplated as would occur to those skilled in the art.

Flange ring 70 is secured to proximal end 54, and a cap member 200 is positioned on flange ring 70. Cap member 200 is secured to flange ring 70 via a spring clip or the like. Flange ring 70 includes a sleeve member 72 defining a cannula bore extending through flange ring 70 for receiving cannula 50 in a snug fitting relationship. Flange ring 70 can then be welded, bolted or otherwise secured to cannula 50. A flange member 74 extends outwardly from sleeve member 72 and is positioned at a proximal end of sleeve member 72 so that flange member 74 is aligned with the proximal end opening of cannula 50. Flange member 74 has a sidewall 75 that includes a groove 76 (FIG. 4) formed therein. Flange member 74 has a flange extension 78 extending therefrom towards the distal end of sleeve member 72. Flange extension 78 has a lock pin hole 79 extending therethrough and also through sleeve member 72 to communicate with working channel 52. Lock pin 95 is selectively positionable in lock pin hole 79 to engage and disengage distractor assembly 80 from cannula 50.

Cap member 200 has a housing 202 and an access port 204 alignable with a corresponding one of the working channel portions 52a and 52b. In the illustrated embodiment, access port 204 is aligned by rotating cap member 200 about the proximal end of cannula 50. It should be understood that other types of cap members for sealing working channel 52 are also contemplated herein. See, for example, the laparascopic instrument and valve described in PCT International Publication No. WO 97/30666, which publication is incorporated herein by reference in its entirety. In the illustrated embodiment of FIG. 1, access port 204 is aligned with working channel portion 52a. Access port 204 provides the surgeon access to at least a portion of working channel 52 to perform surgical procedures. A valve member, such as a disc valve, a duckbill valve, or other valve type known to those skilled in the art, is positioned inside housing 202 to sealingly close access port 204 and maintain the sealed working channel 52. Further, the access port may include an O-ring or the like extending around the instrument opening to sealingly receive instruments extending through access port 204 while maintaining a sealed working channel 52.

Figure 8:
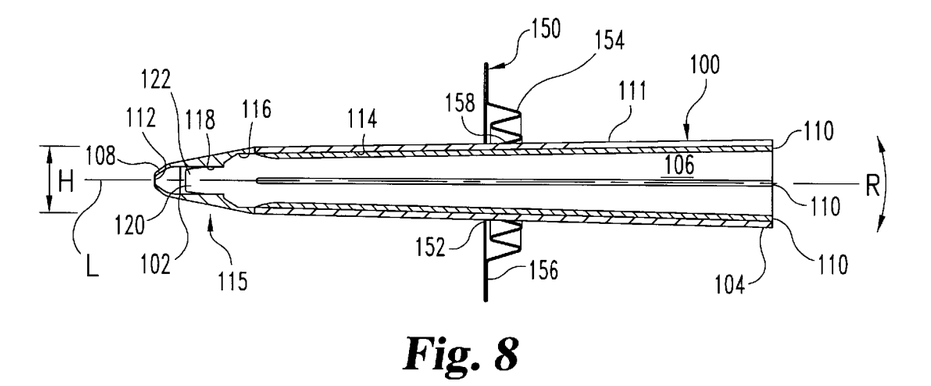
FIG. 8 is a cross-sectional view taken through line 8—8 of FIG. 7.
Figure 9:
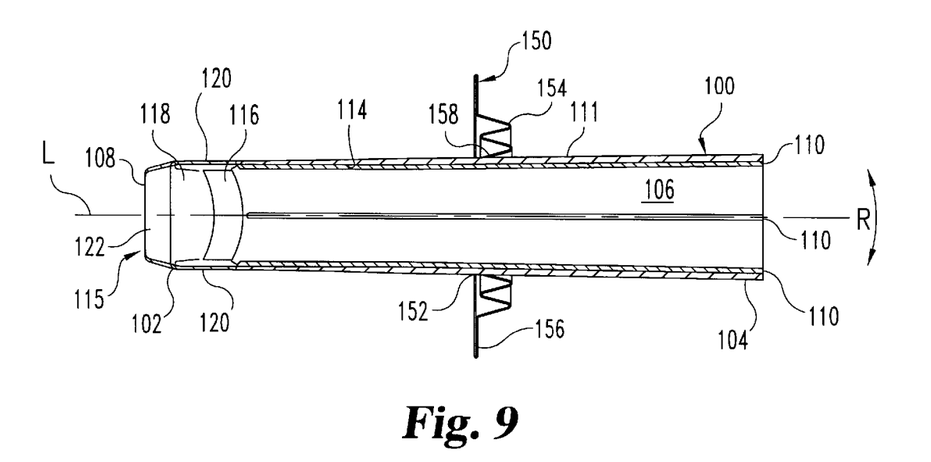
FIG. 9 is a cross-sectional view taken through line 9—9 of FIG. 7.

Referring further to FIGS. 8 and 9, another aspect of sleeve 100 will now be described. At distal end 102 there is provided a receiving portion 115. Receiving portion 115 includes an inner wall formed to conform to the profile of the distal portion of the member that is inserted into sleeve 100. Sleeve 100 can be formed using the member as the mold for the inner wall profile. Receiving portion 115 provides a snug fit with the profile of the distal end portion of the member and sleeve 100, preventing binding or twisting of sleeve 100 while maintaining the protective covering over the distal end portion of the member. Preferably, outer wall 111 of sleeve 100 maintains a smooth profile along the length of sleeve 100 to facilitate insertion.

In the illustrated embodiment, receiving portion 115 is configured to conform to the distal end portion of cannula 50 and distractor assembly 80. Instrument receiving portion 115 includes a distractor shaft contacting portion 116 for contacting the portion of the distractor shafts 84, 94 of distractors 82, 92 extending beyond the distal end 56 of cannula 50. A distractor tip contacting portion 118 extends from shaft contacting portion 116 to distal end wall 108 and defines a nose portion 122. Tip contacting portion 118 contacts the top and bottom of distractor tips 83, 93 extending into nose portion 122. As shown in FIG. 8, receiving portion 115 has a height H that tapers from shaft contacting portion 116 to a reduced height at distal end wall 108. Distraction finger contacting portion 120 is provided along the sides of sleeve 100 for contacting and receiving distraction fingers 58a, 58b. As shown in FIG. 9, sleeve 100 has a width W that tapers from the distal tips of distraction fingers 58a, 58b to a reduced width at distal end wall 108.

In one specific use of apparatus 45 and 45', cannula 50 and distractor assembly 80 are placed through lumen 106 of sleeve 100 until distractor tips 83, 93 are adjacent distal end wall 108. The patient is prepared for laparoscopic spinal procedure and an incision is made for insertion of apparatus 45. In procedures using apparatus 45', flange member 150 is placed around the incision. Sleeve 100, cannula 50 and distractor assembly 80 are inserted through the incision to a location adjacent the disc space. Insertion can be performed, confirmed, and/or monitored endoscopically, radiographically, or under direct vision.

Figure 2:
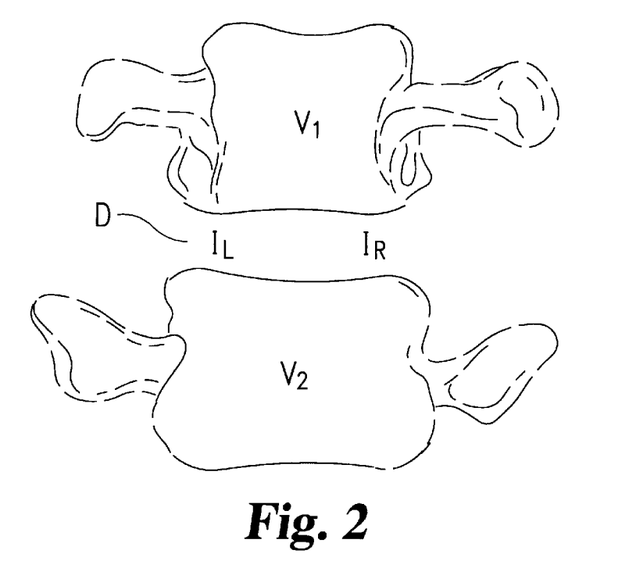
FIG. 2 is a view of a spinal column segment looking from an anterior approach.

Sleeve 100 provides a protective barrier between the skin and tissue and cannula 50 and distractor assembly 80. Cannula 50 and distractor assembly 80 are moved distally relative to sleeve 100 and pushed through distal end wall 108 for insertion of distractor tips 83, 93 and fingers 58a, 58b into the disc space using an impactor cap or known techniques. Once the disc space is distracted to the desired height, distractors 82, 92 can be removed simultaneously or alternately from working channel 52 and procedures performed in the disc space through cannula 50 under sealed working environment provided by cap member 200 and, in procedures using assembly 45', flange member 150. The configuration of cannula 50 allows surgical procedures to be performed within disc space D in order to, for example, prepare the disc space and insert vertebral implants at a left bilateral location $I_L$ and a right bilateral location $I_R$ (FIG. 2.)

Another alternate embodiment and technique, a sleeve 100' similar to sleeve 100 is provided with a thin-wall so that sleeve 100' is flaccid. Sleeve 100' is rolled up on a rod and inserted through a port of an instrument, such as a cannula or rigid sleeve that is already inserted into skin and tissue in a laparoscopic procedure. Alternatively, sleeve 100' can be rolled up on a rod and inserted directly through a skin incision. The flaccid sleeve 100' assumes and retains a reduced size configuration as it is inserted. With sleeve 100' at the desired position, the instrument, if used, and rod are withdrawn leaving sleeve 100' in the incision in its reduced size configuration. An elongate member, such as cannula 50 and distractor assembly 80, is placed through the proximal opening of sleeve 100' into lumen 106', returning sleeve 100' from its reduced size configuration to a shape conforming to the shape of the elongate member as it proceeds through lumen 106'.

While the invention has been illustrated and described in detail in the drawings and foregoing description, the same is to be considered as illustrative and not restrictive in character, it being understood that only the preferred embodiments has been shown and described and that all changes and modifications the come within the spirit of the invention are desired to be protected.

What is claimed is:

1. An apparatus for performing laparoscopic surgical procedures through a tissue opening in a patient, comprising:
   an elongate member with a length extending between a distal end and a proximal end, said elongate member having an outer shape along said length; and
   a sleeve having a proximal end, a distal end, and an inner wall defining a lumen extending between said proximal end and said distal end, said lumen opening at said proximal end to receive said elongate member, said sleeve being resilient and conformable to said outer shape of at least a distal portion of said elongate member, said sleeve further including at least one rib extending from said inner wall into said lumen.

2. The apparatus of claim 1, wherein said at least one rib extends along at least a portion of the length of said sleeve.

3. The apparatus of claim 1, wherein said sleeve is substantially non-expandable.

4. The apparatus of claim 1, wherein said distal end of said sleeve includes a distal end wall having perforations.

5. The apparatus of claim 1, further comprising a flange member defining an opening for receiving said sleeve therethrough, said flange member positionable against the tissue of the patient to seal the tissue opening.

6. The apparatus of claim 5, wherein said sleeve is slidably received in said flange member opening.

7. An apparatus for performing laparoscopic surgical procedure through a tissue opening in a patient, comprising:
   an elongate member with a length extending between a distal end and a proximal end, said elongate member having an outer shape along said length;
   a stretchable, resilient sleeve having a proximal end, a distal end, and an inner wall defining a lumen extending between said proximal end and said distal end, said lumen opening at said proximal end to receive said elongate member; and
   a flange member having an opening slidably and sealingly receiving said sleeve member therethrough, said flange member positionable against the patient to seal the tissue opening.

8. The apparatus of claim 7, wherein said sleeve is conformable to said outer shape of at least a distal portion of said elongate member.

9. The apparatus of claim 7, wherein said distal end includes a distal end wall having means for opening said end wall to allow extension of said elongate member therethrough.

10. The apparatus of claim 7, wherein said flange member includes a corrugated portion about said sleeve and a substantially rigid bearing portion extending outwardly from said corrugated portion.

11. An apparatus for performing laparoscopic surgical procedures through a tissue opening in a patient, comprising:
   an elongate member with a length extending between a distal end and a proximal end, said elongate member having an outer shape and defining a working channel along said length;
   a substantially non-expandable sleeve having a proximal end, a distal end wall, and a lumen extending therebetween opening at said proximal end to receive said elongate member, said sleeve being resilient and conformable to said outer shape of at least a distal portion of said elongate member; and
   a distractor assembly in said working channel, said distractor assembly having at least one tip positionable against said distal end wall of said sleeve.

12. The apparatus of claim 11, wherein said working channel includes a first portion and an adjacent second portion, said first and second portions each configured to receive surgical instruments therethrough.

13. The apparatus of claim 12, wherein said distractor assembly includes a pair of distractor tips positionable against said distal end wall.

14. The apparatus of claim 13, wherein said elongate member includes a pair of fingers extending from said distal end of said elongate member, said pair of distractor tips positionable between said pair of fingers.

15. The apparatus of claim 11, further comprising a cap member substantially sealing said working channel secured to said proximal end of said elongate member.

16. The apparatus of claim 15, further including a flange ring at said proximal end of said elongate member and said cap member is secured to said flange ring.

17. The apparatus of claim 11, wherein:
said elongate member has a racetrack shaped perimeter; and
said sleeve has an inner wall defining said lumen, said inner wall defining said lumen having a racetrack shape conformable to said racetrack shaped perimeter of said elongate member.

18. The apparatus of claim 11, wherein said sleeve further includes at least one rib extending from said inner wall into said lumen.

19. The apparatus of claim 18, wherein said at least one rib includes six ribs extending along at least a portion of the length of said sleeve.

20. The apparatus of claim 11, wherein said distal end wall of said sleeve includes perforations.

21. The apparatus of claim 11, further comprising a flange member defining an opening for receiving said sleeve therethrough, said flange member positionable against the tissue of the patient to seal the tissue opening.

22. The apparatus of claim 21, wherein said sleeve is slidably received in said flange member opening.

23. An apparatus for performing laparoscopic surgical procedures through a tissue opening in a patient, comprising:
an elongate member with a length extending between a distal end and a proximal end, said member having an outer shape along said length; and
a sleeve having a proximal end, a distal end wall, and an inner wall defining a lumen extending between said proximal end and said distal end, said lumen opening at said proximal end to receive said elongate member, said sleeve being resilient and conformable to said outer shape of at least a distal portion of said elongate member, said sleeve further including at least one rib extending from said inner wall into said lumen, wherein said distal end of said sleeve includes a distal end wall having perforations.

24. The apparatus of claim 23, wherein said at least one rib extends along at least a portion of the length of said sleeve.

25. The apparatus of claim 23, wherein said sleeve is stretchable.

26. The apparatus of claim 23, wherein said distal end wall is a thin wall structure.

27. The apparatus of claim 23, further comprising a flange member defining an opening for receiving said sleeve therethrough, said flange member positionable against the patient to seal the tissue opening.

28. The apparatus of claim 27, wherein said sleeve is slidably received in said flange member opening.

29. An apparatus for performing laparoscopic surgical procedures through a tissue opening in a patient, comprising:
an elongate member with a length extending between a distal end and a proximal end, said elongate member having an outer shape along said length;
a sleeve having a proximal end, a distal end, and an inner wall defining a lumen extending between said proximal end and said distal end, said lumen opening at said proximal end to receive said elongate member, said sleeve being conformable to said outer shape of at least a distal portion of said elongate member, said distal end wall including means for opening said end wall to allow extension of said elongate member therethrough, wherein said sleeve further includes at least one rib extending from said inner wall into said lumen to facilitate sliding movement of said sleeve with respect to said elongate member.

30. The apparatus of claim 29, wherein said means for opening includes perforations.

31. The apparatus of claim 29, wherein said means for opening includes a thin wall structure.

32. The apparatus of claim 29, wherein said sleeve is resilient and substantially non-expandable.

33. The apparatus of claim 29, wherein said at least one rib includes six ribs spaced about said inner wall.

34. The apparatus of claim 29, wherein said at least one rib extends along at least a portion of the length of said sleeve.

35. An apparatus for performing laparoscopic surgical procedures through a tissue opening in a patient, comprising:
an elongate member with a length extending between a distal end and a proximal end, said elongate member having an outer shape along said length;
a sleeve having a proximal end, a distal end, and an inner wall defining a lumen extending between said proximal end and said distal end, said lumen opening at said proximal end to receive said elongate member; and
a flange member having an open slidably and sealingly receiving said sleeve member therethrough, said flange member positionable against the patient to seal the tissue opening, wherein said flange member includes a corrugated portion about said sleeve and a substantially rigid bearing portion extending outwardly from said corrugated portion.

36. The apparatus of claim 35, wherein said sleeve is conformable to said outer shape of at least a distal portion of said elongate member.

37. The apparatus of claim 35, wherein said distal end includes a distal end wall having means for opening said end wall to allow extension of said elongate member therethrough.

38. An apparatus for performing laparoscopic surgical procedures through a tissue opening in a patient, comprising:
an elongate member with a length extending between a distal end and a proximal end, said member having an outer shape along said length; and
a sleeve having a proximal end, a distal end wall, and an inner wall defining a lumen extending between said proximal end and said distal end, said lumen opening at said proximal end to receive said elongate member, said sleeve being stretchable to conform to said outer shape of at least a distal portion of said elongate member when said distal end of said elongate member is in contact with said distal end wall of said sleeve, said distal end wall including means for opening said end wall to allow extension of said elongate member therethrough.

39. The apparatus of claim 38, wherein said elongate member defines a working channel extending along said length.

40. The apparatus of claim 39, wherein said working channel includes a first portion and an adjacent second portion, said first and second portions each configured to receive surgical instruments therethrough.

41. The apparatus of claim 40, further comprising a distractor assembly in said working channel of said elongate member, said distractor assembly including a pair of distractor tips positionable against said distal end wall.

42. The apparatus of claim 41, wherein said elongate member includes a pair of fingers extending from said distal end of said elongate member, said distractor tips positioned between said pair of fingers.

43. The apparatus of claim 40, further comprising a cap member substantially sealing said working channel secured to said proximal end of said elongate member.

44. The apparatus of claim 43, further including a flange ring at said proximal end of said elongate member and said cap member is secured to said flange ring.

45. The apparatus of claim 38, wherein:
said elongate member has a racetrack shaped perimeter; and
said sleeve has an inner wall defining said lumen, said inner wall defining said lumen having a racetrack shape conformable to said racetrack shaped perimeter of said elongate member.

46. The apparatus of claim 38, wherein said sleeve further includes at least one rib extending from said inner wall into said lumen.

47. The apparatus of claim 46, wherein said at least one rib includes six ribs extending along at least a portion of the length of said sleeve.

48. The apparatus of claim 38, further comprising a flange member defining an opening for receiving said sleeve therethrough, said flange member positionable against the tissue of the patient to seal the tissue opening.

49. The apparatus of claim 48, wherein said sleeve is slidably received in said flange member opening.

50. The apparatus of claim 38, wherein said means for opening includes perforations.

51. The apparatus of claim 38, wherein said means for opening includes a thin wall structure.

52. The apparatus of claim 38, wherein said sleeve is resilient and substantially non-expandable.

53. A method for performing a laparoscopic surgical procedure at a location in a patient, comprising:
providing a tissue opening in the patient;
providing an elongate member with a length extending between a distal end and a proximal end, said elongate member having an outer shape along said length, and a sleeve having a proximal end, a distal end wall, and a lumen extending therebetween opening at said proximal end receiving at least a distal portion of said elongate member, said sleeve being resilient and conformable to said outer shape of at least the distal portion of said elongate member;
providing a flange member having a central opening for receiving the sleeve;
placing the elongate member and sleeve through the flange member;
placing the elongate member and the sleeve into the tissue opening;
sealing the space between the tissue and the sleeve with the flange member; and
advancing the sleeve and elongated member into the sealed space.

54. The method of claim 53, further comprising:
advancing the elongate member through the distal end wall of the sleeve to the location.

55. The method according to claim 54, wherein:
providing the elongate member includes providing the elongate member with a working channel extending between the proximal and distal end; and
further comprising performing a procedure at the location through the working channel.

56. A method for performing a laparoscopic surgical procedure through skin and tissue of a patient, comprising:
incising the skin and tissue of the patient;
providing an elongate member with a length extending between a distal end and a proximal end, the elongate member having an outer shape along its length, and a sleeve having a proximal end, a distal end wall, and a lumen extending therebetween opening at the proximal end receiving at least a distal portion of the elongated member, the sleeve being substantially made from a resilient material and conformable to the outer shape of at least the distal portion of the elongate member;
providing a flange member having a central opening receiving the sleeve therethrough;
placing the flange member on the skin; and
advancing the elongate member and sleeve through the flange member and through the incision to the spine while the sleeve provides a barrier between the tissue and the elongate member.

57. The method of claim 56, wherein providing the elongate member includes providing the elongate member with a working channel extending between the proximal end and the distal end and opposite fingers extending from the distal end of the elongate member.

58. The method of claim 57, further comprising providing a distractor assembly positioned in the working channel and secured to the sleeve, the distractor assembly including at least one distractor tip positioned between the opposite fingers.

59. The method of claim 58, further comprising:
advancing the elongate member and distractor assembly through the distal end wall of the sleeve into a disc space of the spine.

60. The method of claim 56, wherein the flange member seals the space between the tissue and the sleeve.

* * * * *